United States Patent
Leitch

(10) Patent No.: US 10,524,834 B2
(45) Date of Patent: Jan. 7, 2020

(54) OBSTETRICAL INSTRUMENT

(71) Applicant: DAYLIGHT OB, LLC, Fort Wayne, IN (US)

(72) Inventor: Rosemary E. Leitch, Fort Wayne, IN (US)

(73) Assignee: DAYLIGHT OB, LLC, Fort Wayne, IN (US)

( * ) Notice: Subject to any disclaimer, the term of this patent is extended or adjusted under 35 U.S.C. 154(b) by 176 days.

(21) Appl. No.: 15/463,854

(22) Filed: Mar. 20, 2017

(65) Prior Publication Data

US 2017/0189067 A1    Jul. 6, 2017

Related U.S. Application Data

(63) Continuation-in-part of application No. 15/212,834, filed on Jul. 18, 2016, now abandoned, which is a continuation of application No. 13/904,528, filed on May 29, 2013, now Pat. No. 9,408,633.

(60) Provisional application No. 61/689,357, filed on Jun. 5, 2012.

(51) Int. Cl.
  *A61B 17/44* (2006.01)
  *A61B 17/42* (2006.01)
  *A61B 17/00* (2006.01)

(52) U.S. Cl.
  CPC ............ *A61B 17/442* (2013.01); *A61B 17/42* (2013.01); *A61B 2017/00022* (2013.01); *A61B 2017/00221* (2013.01); *A61B 2017/00429* (2013.01); *A61B 2017/00473* (2013.01); *A61B 2017/00946* (2013.01); *A61B 2017/445* (2013.01)

(58) Field of Classification Search
  CPC ... A61B 17/42; A61B 17/442; A61B 17/4208; A61B 17/44; A61B 2017/00022; A61B 2017/00221; A61B 2017/00429; A61B 2017/00473; A61B 2017/00946; A61B 2017/445; A61B 2017/4225; A61B 2017/4216; A61B 2017/4233; A61B 2017/447
  See application file for complete search history.

(56) References Cited

U.S. PATENT DOCUMENTS

| 1,780,155 | A |   | 11/1930 | Hahn |
|---|---|---|---|---|
| 4,483,636 | A | * | 11/1984 | Meyer ................. A45D 34/04 132/320 |
| 5,388,700 | A |   | 2/1995 | Per-Lee |
| 5,846,181 | A | * | 12/1998 | Heckele ............ A61B 1/00073 600/104 |
| 5,870,792 | A |   | 2/1999 | Shurtliff |

(Continued)

FOREIGN PATENT DOCUMENTS

WO    2011038310    3/2011

OTHER PUBLICATIONS

Keisha A. Jones et al., Pessary Use in Pelvic Organ Prolapse and Urinary Incontinence, vol. 3 No. 1 2010 Reviews N Obstetrics & Gynecology.

(Continued)

*Primary Examiner* — Jocelin C Tanner
(74) *Attorney, Agent, or Firm* — Faegre Baker Daniels LLP

(57) ABSTRACT

An obstetrical instrument includes an elongated handle and a fetal head support portion coupled with a distal end of the elongated handle.

22 Claims, 17 Drawing Sheets

(56) References Cited

U.S. PATENT DOCUMENTS

| | | | |
|---|---|---|---|
| 5,935,136 A * | 8/1999 | Hulse .................... | A61B 17/442 606/119 |
| 6,438,787 B1 | 8/2002 | Young | |
| 2003/0105388 A1* | 6/2003 | Roy ..................... | A61B 5/0031 600/300 |
| 2006/0161175 A1* | 7/2006 | Ross .................... | A61B 17/442 606/123 |
| 2008/0216272 A1 | 9/2008 | McLain | |
| 2009/0204124 A1* | 8/2009 | Ross .................... | A61B 17/442 606/123 |
| 2009/0254096 A1* | 10/2009 | Porat .................... | A61B 5/0011 606/123 |
| 2010/0106150 A1* | 4/2010 | Thompson ............. | A61B 18/08 606/29 |
| 2010/0305406 A1* | 12/2010 | Braun .................... | H01C 7/006 600/202 |
| 2011/0196382 A1 | 8/2011 | Barrier et al. | |
| 2011/0218547 A1* | 9/2011 | Ishii ..................... | A61B 17/442 606/123 |

OTHER PUBLICATIONS

Anthony J. Viera et al., Practical Use of the Pessary, American Family Physician, May 1, 2000.
C-Snorkel, Clinical Inovations, dated 2012, available at http://www.pertormance-mastermedical.com/Product_Line/OB-GYN/C-Snorkel%20Brochure.pdf.

* cited by examiner

OBSTETRICAL INSTRUMENT

CROSS-REFERENCE TO RELATED APPLICATIONS

This application is a continuation-in-part application of U.S. application Ser. No. 15/212,834, filed Jul. 18, 2016, which is a continuation of U.S. application Ser. No. 13/904,528, filed May 29, 2013, issued as U.S. Pat. No. 9,408,633, which claims priority to U.S. Provisional Patent Application No. 61/689,357, filed Jun. 5, 2012, the disclosures of each of which are hereby incorporated by reference in their entirety.

FIELD OF THE DISCLOSURE

The present disclosure relates generally to an obstetrical instrument, and, more particularly, to an obstetrical instrument for use during the birthing process

DESCRIPTION OF THE RELATED ART

It is not uncommon during the birthing process for a pregnant patient to reach full dilation of the cervix and begin pushing the fetus down through the birth canal only to have the fetus become lodged in the birth canal. Often a vacuum or forceps may be used to further assist the delivery. This may, however, worsen the situation by causing the fetus to become more firmly impacted or lodged in the birth canal without achieving delivery. After attempts of vaginal delivery are abandoned, the delivering physician must deliver the fetus through cesarean section.

During the course of a cesarean section, the fetus must be positioned such that the physician can reach behind the head of the fetus to deliver the baby out of the uterine cavity through an incision made for purposes of delivery. Presently, the fetal head is often positioned for such delivery by an assisting physician or nurse. Such an assistant must insert his or her hand up through the birth canal and place his or her fingers against the fetal head to position the head such that the delivering physician can reach behind the head and gently deliver the baby out through the incision in the uterine cavity. Often in such cases, a surgical drape is placed over the legs of the patient and the assistant is essentially working blind under the sterile drape.

The assistant who asserts the force to push the fetal head into position for the delivering physician does so with his or her fingers, which requires considerable force and is limited by the length of the assistant's arms and/or fingers, as well as by the assistant's physical strength.

Improvements in the foregoing are desired.

SUMMARY

The present disclosure provides an obstetrical instrument, namely, a fetal head elevator, including an elongated handle and a fetal head support portion coupled with a distal end of the elongated handle.

The disclosure further provides an obstetrical instrument, namely, a fetal head elevator including an elongated handle, an intermediate member coupled with a distal end of the elongated handle, and a fetal head support portion coupled with the intermediate member.

Additionally, the present disclosure further provides a method of repositioning the head of a fetus during the birthing process. According to the method of the present invention, an obstetrical instrument, namely a fetal head elevator, is provided which includes an elongated handle and a fetal head support portion coupled with a distal end of the elongated handle. A distal end of the obstetrical instrument, namely the fetal head elevator, is inserted into the birth canal of a patient and is positioned such that the fetal head support portion of instrument is directly adjacent to the head of the fetus. A controlled pressure is then applied against the fetal head to reposition the fetal head from birth canal into the uterine cavity.

In one exemplary embodiment, an obstetrical instrument is provided. The obstetrical instrument includes an elongated handle and a flared portion extending from said elongated handle. The flared portion has a distal face defining a perimeter, the distal face sized and structured to support and elevate a fetal head. The flared portion defines a fluid flow path from the distal face to an exterior of the flared portion, such that, with the obstetrical instrument positioned to support and elevate the fetal head, a fetal head elevating force transmitted through the obstetrical instrument is spread across the distal face of the flared portion. The fluid flow path presents a gap in the distal face within the perimeter of the flared portion, the gap defining an area within the perimeter that does not contact the fetal head. The gap resists formation of a vacuum between the flared portion and a fetal head supported by the obstetrical instrument. The instrument further includes a pressure sensor positioned to measure the fetal head elevating force applied to the fetal head by the obstetrical instrument. In a more particular embodiment, the pressure sensor comprises a plurality of pressure pads positioned on the distal face of the flared portion.

In an exemplification, the distal face can provide a contact area of about 7.4 in$^2$ (4774 mm$^2$). In alternative embodiments, the distal face can provide a contact area of about 7.0 in$^2$ (4516 mm$^2$), about 7.1 in$^2$ (4581 mm$^2$), about 7.2 in$^2$ (4645 mm$^2$), about 7.3 in$^2$ (4710 mm$^2$), about 7.4 in$^2$ (4774 mm$^2$), about 7.5 in$^2$ (4839 mm$^2$), about 7.6 in$^2$ (4903 mm$^2$), about 7.7 in$^2$ (4968 mm$^2$), about 7.8 in$^2$ (5032 mm$^2$), or about or any range within any two of the foregoing values. In one particular embodiment, the distal face is in the form of a sphere cap with dimensions r=177.8 mm, h=4.6 mm and a=40 mm, with "r" denoting the radius of the sphere, "a" denoting the measure of the base radius of the plane intersecting the sphere and defining the sphere cap and "h" denoting the height of the sphere cap. For clarity, these dimensions are marked in FIG. 17. In this embodiment, the distal face would provide an area of 7.9 in$^2$ (5093 mm$^2$) if it were not interrupted. In an exemplification, the distal face is interrupted by 4 holes extending through the distal face, with each hole removing 0.13 in$^2$ (81.7 mm$^2$) of the distal face contact area, yielding an available distal face contact area of 4766 mm$^2$ (about 7.4 in$^2$). In spherical embodiments, the radius of the sphere may be, for example, 60 mm or 80 mm. The dimensions mentioned in this paragraph are merely exemplary and are not meant to be limiting in any way. In certain embodiments, interchangeable heads with differing contact areas may be provided in different colors to facilitate selection based on maternal and fetal habitus. In one-piece embodiments, color may similarly be used to denoted fetal contact area size across a family of differently sized instruments.

In one more particular embodiment, the obstetrical instrument includes a battery and a transmitter operatively coupled to the pressure sensor and configured to be positioned in an interior cavity of the elongated handle. The transmitter is configured to wirelessly transmit a signal indicating the measured pressure to an external receiver.

In another more particular embodiment, the obstetrical instrument includes a wire extending through a conduit from the pressure sensor to a proximal end of the elongated handle. The wire is configured to transmitting a signal indicating the measured pressure from the pressure sensor to an external receiver.

In a more particular embodiment of any of the above embodiments, the elongated handle includes a recessed groove extending from the flared portion along an upper portion of the elongated handle. In another more particular embodiment of any of the above embodiments, the elongated handle includes a grip portion having a plurality of grooves defined between a plurality of circumferential ridges, the recessed groove extending from the flared portion through at least a portion of the grip portion. In another more particular embodiment of any of the above embodiments, the elongated handle includes at least one directional indicator selected from the group consisting of: a recessed groove extending from the flared portion along an upper portion of the elongated handle; a depression in the elongated handle configured to receive a user's thumb; and a plurality of indexing markers positioned on a plurality of ridges of the elongated handle. In another more particular embodiment of any of the above embodiments, the elongated handle includes a bulbous portion, at least a portion of the bulbous portion having a plurality of grooves defined between a plurality of circumferential ridges. In another more particular embodiment of any of the above embodiments, the flared portion is rotatably affixed to the elongated handle, In another more particular embodiment of any of the above embodiments, the elongated handle includes a conduit, wherein the conduit defines a fluid passageway extending from a distal end of the elongated handle to a proximal end of the elongated handle.

In another exemplary embodiment, an obstetrical instrument is provided. The obstetrical instrument includes an elongated handle and a flared portion extending from said elongated handle. The flared portion has a distal face defining a perimeter, the distal face sized and structured to support and elevate a fetal head. The flared portion defines a fluid flow path from the distal face to an exterior of the flared portion, such that, with the obstetrical instrument positioned to support and elevate the fetal head, a fetal head elevating force transmitted through the obstetrical instrument is spread across the distal face of the flared portion. The fluid flow path presents a gap in the distal face within the perimeter of the flared portion, the gap defining an area within the perimeter that does not contact the fetal head. The gap resists formation of a vacuum between the flared portion and a fetal head supported by the obstetrical instrument. The elongated handle includes at least one directional indicator. In one more particular embodiment, the directional indicator includes a recessed groove extending from the flared portion along the upper portion of the elongated handle. In another more particular embodiment of any of the above embodiments, the directional indicator includes a depression in the elongated handle configured to receive the user's thumb. In another more particular embodiment of any of the above embodiments, the directional indicator includes a plurality of indexing markers positioned on a plurality of ridges of the elongated handle. In another more particular embodiment of any of the above embodiments, the flared portion is rotatably affixed to the elongated handle, In another more particular embodiment of any of the above embodiments, the elongated handle includes a conduit defining a fluid passageway extending from a distal end of the elongated handle to a proximal end of the elongated handle.

In another exemplary embodiment, an obstetrical instrument is provided. The obstetrical instrument includes an elongated handle and a flared portion extending from said elongated handle. The flared portion is rotatably affixed to the elongated handle. The flared portion has a distal face defining a perimeter, the distal face sized and structured to support and elevate a fetal head. The flared portion defines a fluid flow path from the distal face to an exterior of the flared portion, such that, with the obstetrical instrument positioned to support and elevate the fetal head, a fetal head elevating force transmitted through the obstetrical instrument is spread across the distal face of the flared portion. The fluid flow path presents a gap in the distal face within the perimeter of the flared portion, the gap defining an area within the perimeter that does not contact the fetal head. The gap resists formation of a vacuum between the flared portion and a fetal head supported by the obstetrical instrument. In a more particular embodiment, the flared portion is rotatably affixed to the elongated handle via a ball and socket joint, In another more particular embodiment of any of the above embodiments, the elongated handle includes a conduit defining a fluid passageway extending from a distal end of the elongated handle to a proximal end of the elongated handle.

In another exemplary embodiment, an obstetrical instrument is provided. The obstetrical instrument includes an elongated handle having a conduit extending from a distal end of the elongated handle to a proximal end of the elongated handle. The obstetrical instrument further includes a flared portion extending from said elongated handle, the flared portion defining a circumference and having a distal face sized and structured to support and elevate a fetal head. The flared portion includes an opening within the circumference of the flared portion, the opening in fluid communication with the conduit defining a fluid flow path through the flared portion and the elongated handle such that, with the obstetrical instrument positioned to support and elevate the fetal head, a fetal head elevating force transmitted through the obstetrical instrument is spread across the distal face of the flared portion and whereby the fluid flow path resists formation of a vacuum between the flared portion and a fetal head supported by the obstetrical instrument.

In another exemplary embodiment, an obstetrical instrument is provided. The obstetrical instrument includes an elongated handle and a flared portion extending from the elongated handle. The flared portion has a distal face sized and structured to support and elevate a fetal head. The obstetrical instrument further includes a suction head including a plurality of openings in fluid communication with a vacuum source, the suction head sized and structured to assist in a vacuum assisted vaginal delivery. In a more particular embodiment, the obstetrical instrument includes a vacuum tube fluidly connecting the suction head with the vacuum source, at least a portion of the vacuum tube being positioned in a conduit extending from a distal end of the elongated handle to a proximal end of the elongated handle. In another more particular embodiment of any of the above embodiments, the flared portion includes a second plurality of openings within a circumference of the flared portion, the second plurality of openings extending from the distal face to a proximal side of the flared portion and defining a fluid flow path therethrough. In another more particular embodiment of any of the above embodiments, the obstetrical instrument includes a depression in the elongated handle configured to receive a user's thumb.

In a further exemplary embodiment, a method of delivering a fetus is provided. The method of this form of the present disclosure includes the step of attempting a vaginal delivery by: inserting a distal end of an obstetrical instrument into a vagina of a patient, the obstetrical instrument comprising: an elongated handle and a flared portion extending from the elongated handle, the flared portion having a distal face, the distal face having a conduit in fluid communication with a vacuum source; and applying a vacuum to the fetus with the obstetrical instrument to facilitate a vaginal delivery. The method continues with the step of discontinuing the step of applying a vacuum to the fetus. Additional steps of the method of this form of the present disclosure include proceeding to a delivery via a cesarean section, comprising the steps of: positioning the flared portion of the obstetrical instrument to support a head of the fetus; and applying a fetal head elevating pressure against the fetal head with the flared portion of the obstetrical instrument to reposition the fetal head through the birth canal into a uterine cavity of the patient.

In alternative forms of the method of delivering a fetus in accordance with the present disclosure, the distal face of the flared portion of the obstetrical instrument defines a contact surface area within the perimeter available to contact the fetal head, the contact surface area larger than an area of the gap, whereby during the step of applying a fetal head elevating pressure against the fetal head, the fetal head elevating pressure is spread across the contact surface area.

In alternative forms of the method of delivering a fetus in accordance with the present disclosure, the obstetrical instrument further comprises a fetal head support portion releasably coupled with the flared portion.

In alternative forms of the method of delivering a fetus in accordance with the present disclosure, the elongated handle of the obstetrical instrument is curved to accommodate a natural curvature of a pelvis.

Advantageously, in some exemplary embodiments, the presently disclosed obstetrical instrument allows for the fetal head to be safely repositioned from the birth canal into the uterine cavity for delivery via cesarean section.

Additionally, in some exemplary embodiments, the presently disclosed obstetrical instrument allows for the fetal head to be elevated, the delivering practitioner is able to easily reach behind the head for a faster delivery than is available without the instrument of the present disclosure and with minimized risk of injury to the fetus and to the patient.

Additionally, in some exemplary embodiments, the presently disclosed obstetrical instrument allows the user to use one or both hands to exert a controlled pressure to slowly elevate the head of the fetus into position for a delivering physician to efficiently and safely deliver the fetus through a cesarean section incision.

BRIEF DESCRIPTION OF THE DRAWINGS

The above-mentioned and other features and advantages of this disclosure, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

Figure 1:
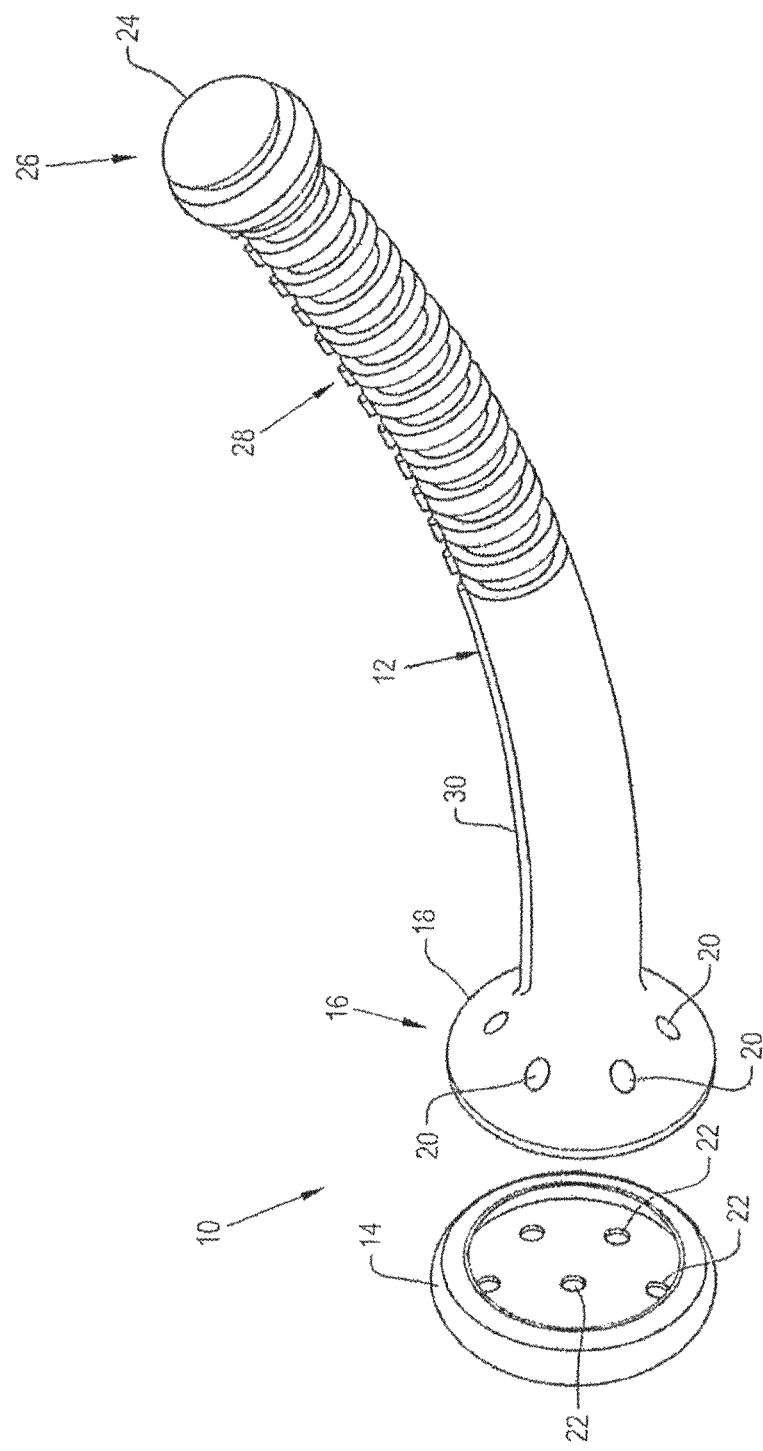
FIG. 1 is a perspective view of an embodiment of an obstetrical instrument according to the present disclosure.
Figure 2:
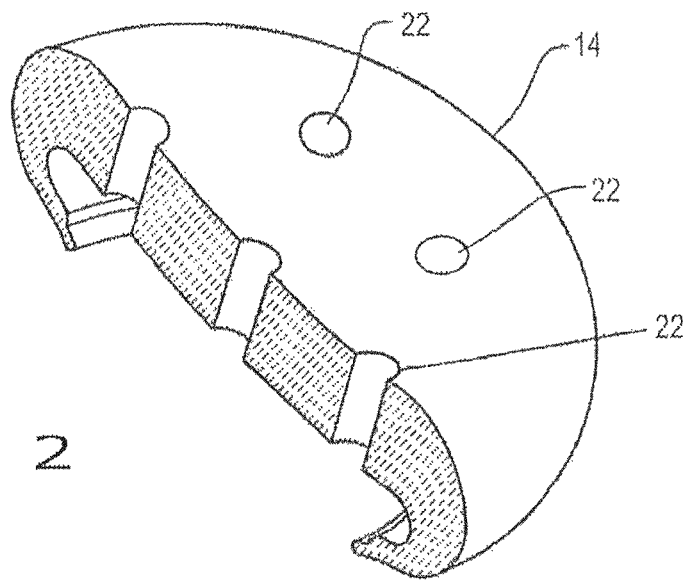
FIG. 2 is a cross-sectional view of a fetal head support portion of the obstetrical instrument of FIG. 1.

Referring now to the drawings, and more particularly to FIGS. 1 and 2, there is shown an obstetrical instrument 10, illustratively a fetal head elevator. As shown in FIGS. 1 and 2, obstetrical instrument 10 includes an elongated handle 12 and a fetal head support portion 14 (shown in cross section in FIG. 2).

At a distal end 16 of handle 12 is a flared portion 18 including a plurality of openings 20 extending through the flared portion 18. Although illustrated as six openings 20 circumferentially spaced around a central axis of flared portion 18, in other embodiments, the plurality of openings 20 may be positioned in other suitable arrangements and may include more or fewer than six openings 20.

Fetal head support portion 14 also includes a plurality of openings 22 extending from a proximal surface to a distal surface of fetal head support portion 14. As illustrated in FIG. 1, the plurality of openings 22 of fetal head support portion 14 are arranged such that when fetal head support portion 14 is coupled with handle 12, one or more of openings 22 of fetal head support portion 14 are aligned with one or more of openings 20 of flared portion 18 such that openings 22 are in fluid connection with the plurality of openings 20. Such a fluid connection allows for a fluid, such as air, to flow freely through the obstetrical instrument 10 such that no vacuum is created between obstetrical instrument 10 and the head of a fetus during use by a practitioner.

Alternatively, or in addition, a groove (not shown) may be formed within flared portion 18 such that it intersects with one or more of the plurality of openings 20 in flared portion 18 of handle 12 such that, regardless of the position of fetal head support portion, the plurality of openings 22 extending therethrough are in alignment with the groove (not shown), and thus in fluid connection with the plurality of openings 20 extending through flared portion 18 of handle 12.

Fetal head support portion 14 is coupled, for example fixedly coupled or releasably coupled, with distal end 16 of elongated handle 12. In the exemplary embodiment illustrated in FIG. 1, fetal head support portion 14 is coupled with flared portion 18. Exemplary mechanisms for coupling distal end 16 of elongated handle 12 with fetal head support portion 14 include the use of an adhesive, corresponding male and female threads (not shown) included on the distal end 16 of elongated handle 12 and fetal head support portion 14, and a fixation ring and/or at least one flange for affixing it to distal end 16 of elongated handle 12.

In one exemplary embodiment, fetal head support portion 14 is formed of a flexible material configured to cushion and support the head of a fetus while obstetrical instrument 10 is in use. The flexible material is illustratively sufficiently flexible or resilient such that damage to the fetal head is avoided despite the application of pressure across the surface area of the fetal head support portion 14. In some exemplary embodiments, the flexible material has a Shore A hardness in a range between approximately 30 and 50. Illustratively, the flexible material comprises a foam having a foam density between approximately 3 and 5 pounds per cubic foot (lb/ft). In some exemplary embodiments, the fetal head support portion 14 may, for example, be formed of or covered with a sterile foam material and/or sponge material. Suitable materials from which the fetal head support portion 14 may be covered with or formed of include polyurethane foam, cotton, rayon, polyester or any resilient antimicrobial foam.

As illustrated in FIG. 1, the fetal head support portion 14 and flared portion 18 are substantially disc-shaped such that when the obstetrical instrument 10 is in use force exerted by the user of the device is spread across the disc's surface area, rather than focused at a single point, such as is the case, for example if a practitioner must use his or her finger(s) to reposition the head of a fetus.

Figure 4:
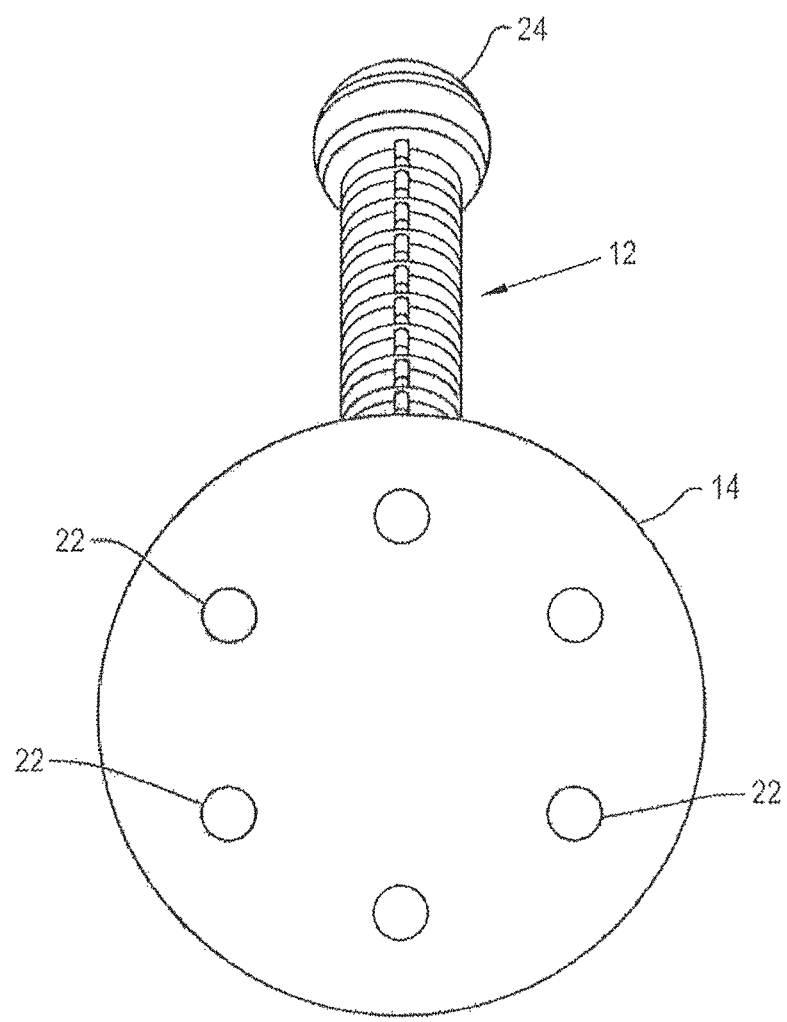
FIG. 4 is an end view of an obstetrical instrument according to the embodiment illustrated in FIG. 1.

Handle 12 of obstetrical instrument 10 may be formed of any material known in the art for surgical instruments. Suitable materials for handle 12 include stainless steel, urethane, silicone, polyurethane, titanium and other surgical grade polymers and metals. As illustrated in FIGS. 1 and 4, elongated handle 12 is formed such that it has a gentle curve from proximal end 26 to distal end 16 to accommodate the natural curvature of a pelvis.

As shown in FIGS. 1 and 4, elongated handle 12 illustratively includes a bulbous portion 24 at a proximal end 26 of handle 12. Bulbous portion 24 advantageously helps to assure that the user's hand does not slip off of obstetrical instrument's 10 handle 12 during use.

Handle 12 illustratively further includes a grip portion 28, which may be in any known configuration in the art which prevents obstetrical instrument 10 from slipping while in use, despite encountering the inevitable moisture from body fluids during the birthing process. As shown in FIG. 1, grip portion 28 illustratively includes a plurality of ridges extending around an outer circumference of handle 12. Handle 12 further includes a ridge 30 extending along a superior aspect of handle 12 in a direction parallel with a longitudinal axis of the elongated handle 12. Ridge 30 serves as a directional indicator to mark the top of the device, thus allowing the individual maneuvering obstetrical instrument 10 to have a tactile sense of the position of the device for situations when a visual sense of position is not feasible, for example, due to the use of a sterile drape during a cesarean section.

Figure 3:
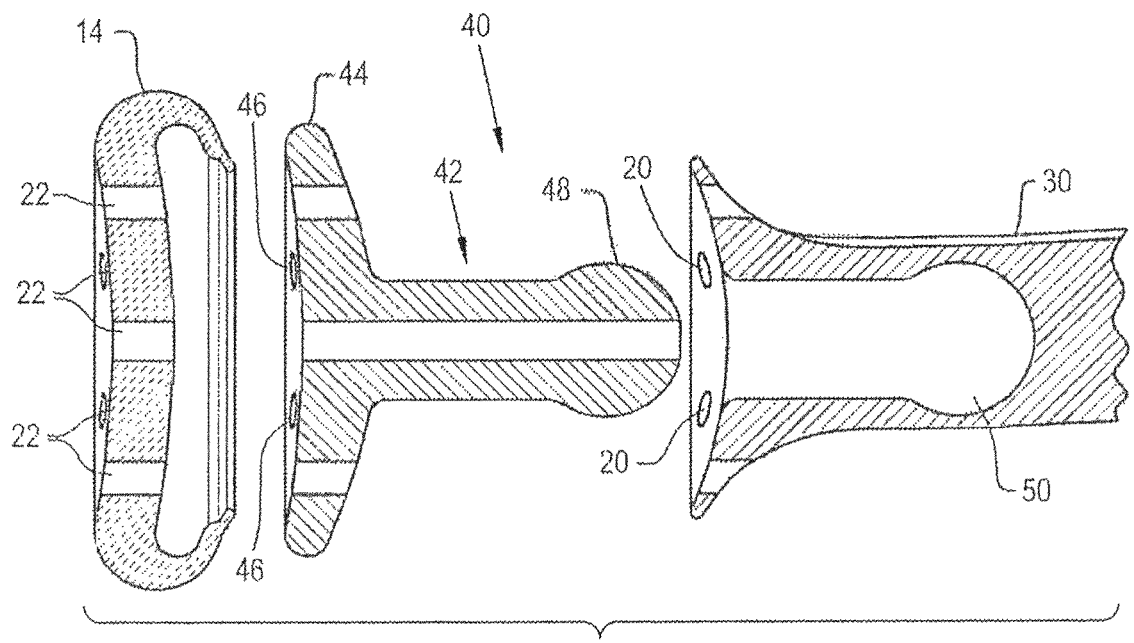
FIG. 3 is an exploded sectional view of another embodiment of an obstetrical instrument according to the present invention.

Referring now to FIG. 3, another obstetrical instrument 40 is illustrated. Obstetrical instrument 40 is similar to obstetrical instrument 10 illustrated in FIG. 1 and may include any or all of the features of obstetrical instrument 10. The same numerals used to refer to components of obstetrical instrument 10 are used to refer to similar components of obstetrical instrument 40. Obstetrical instrument 40 includes intermediate member 42. Intermediate member 42 includes a disc-shaped portion 44 which includes a plurality of openings 46 extending therethrough and which are arranged such that they are in fluid alignment with openings 20 in flared portion 18 of handle and openings 22 in fetal head support portion 14 when assembled. Accordingly, in use, the aligned openings (20, 22 and 46) provide a fluid passage such that no vacuum is created between the obstetrical instrument 40 and the fetal head.

As illustrated in FIG. 3, fetal head support portion 14 is releasably coupled with disc-shaped portion 44 of intermediate member 42. It is, however, feasible for fetal head support portion 14 to be fixedly coupled with disc-shaped portion 44 of intermediate member, for example using an adhesive. When assembled, intermediate member 42 is fixedly or releasably coupled with distal end 16 of handle 12, for example with flared portion 18 of handle 12.

Intermediate member 42 may be firmly coupled with handle 12 using any number of known coupling or fastening mechanisms, for example a key lock system, a cam system or a ball and socket mechanism, such as that illustrated in FIG. 3. According to the embodiment of obstetrical instrument 40 illustrated in FIG. 3, intermediate member 42 includes at its proximal end a ball 48 configured for being received in a corresponding socket 50 formed in handle 12.

Referring now to FIG. 4, there is shown an end view of an obstetrical instrument 10 or 40 which clearly illustrates a plurality of openings 22 in fetal head support portion 14. Although openings 22 are arranged in a generally circular pattern around a central point of the generally disc-shaped fetal head support portion 14, openings 22 may be arranged in any number of ways, as long as they are in fluid communication with corresponding openings in the intermediate member 42 and/or flared portion 18 of handle 12, depending upon the embodiment. The edge of the fetal head support portion 14 which would come into contact with a patient's vaginal mucosa and/or bladder is sufficiently smooth such that it easily slides along the mucosa, thus preventing injury to the bladder and/or vaginal mucosa of the birth canal.

Figure 5:
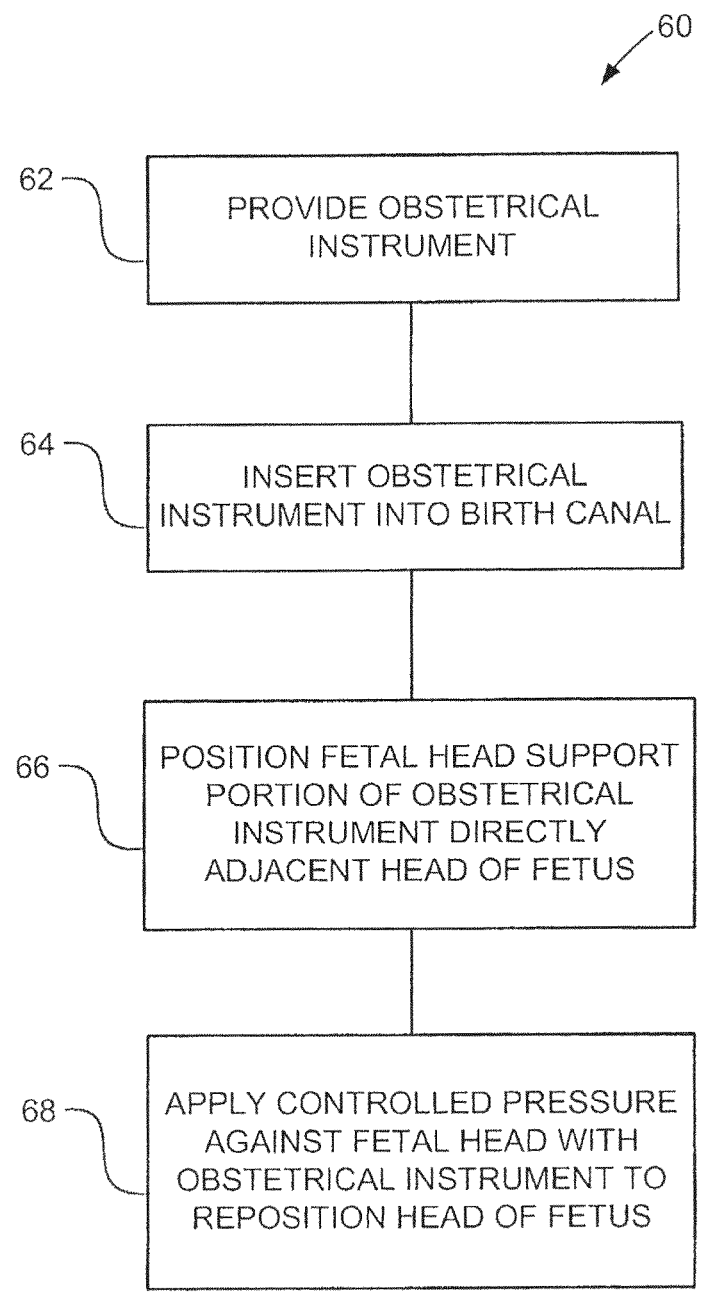
FIG. 5 is a flow chart of a method of repositioning the head of a fetus during the birthing process.

The present invention further provides a method 60 of repositioning the head of a fetus during the birthing process, in other words during childbirth. Referring now to FIG. 5, there is shown a flow chart illustrating the steps of the method 60 according to the present invention. An obstetrical instrument is provided at step 62 which includes an elongated handle and a fetal head support portion coupled with a distal end of the elongated handle. A distal end of the obstetrical instrument is inserted into the birth canal of a patient at step 64. The fetal head support portion of the obstetrical instrument is positioned directly adjacent the head of a fetus at step 66. A controlled pressure is applied against the fetal head with the obstetrical instrument at step 68 to reposition the head of the fetus through the birth canal into the uterine cavity. The obstetrical instrument allows the user to ease the act of elevating the fetal head for purposes of delivery through a cesarean section. More specifically, the obstetrical instrument allows the user to slowly push the fetal head up to the point where a delivering physician can reach below the fetal head and complete the delivery.

Figure 6:
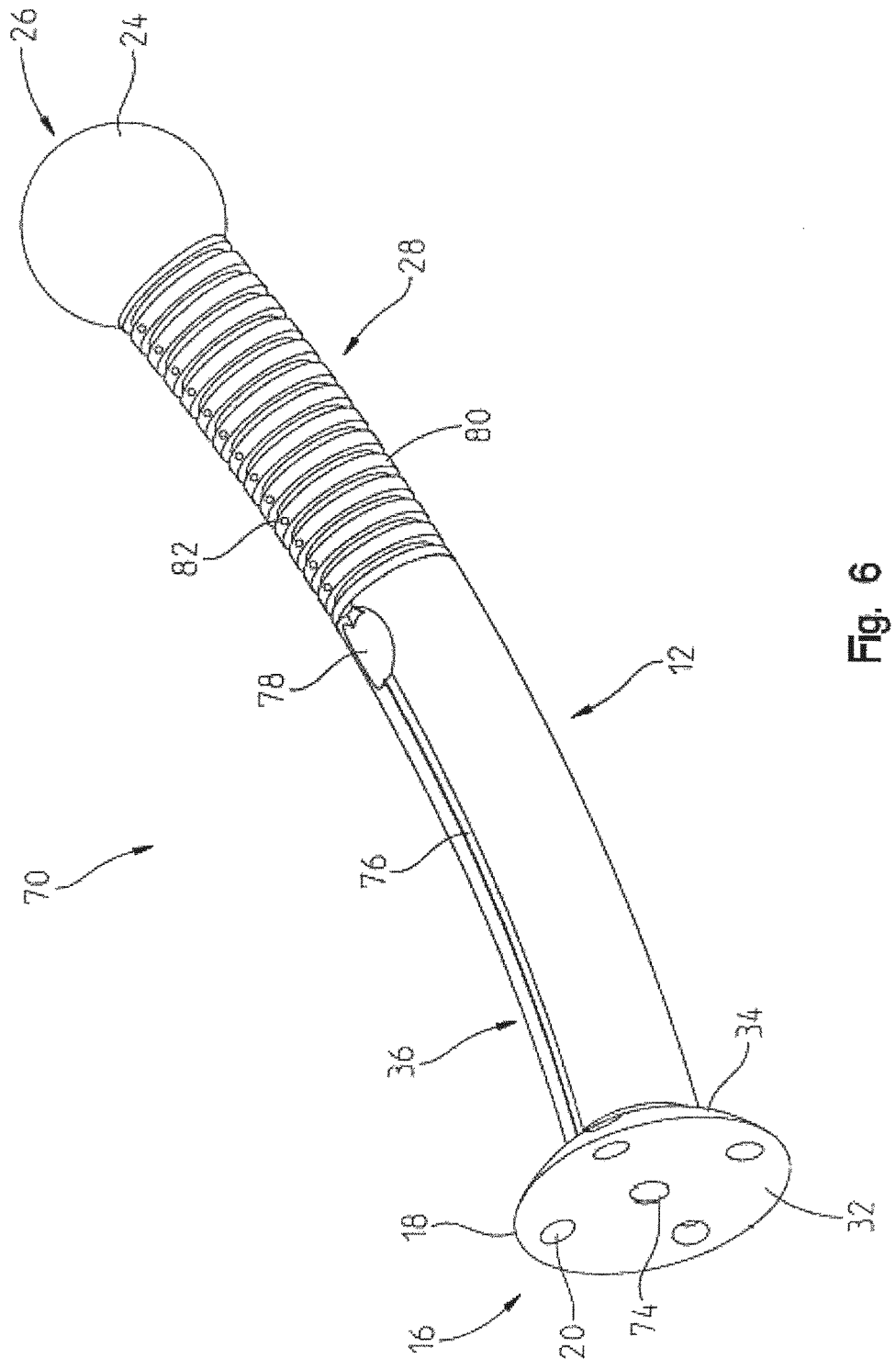
FIG. 6 is a perspective view of still another embodiment of an obstetrical instrument according to the present disclosure.
Figure 7:
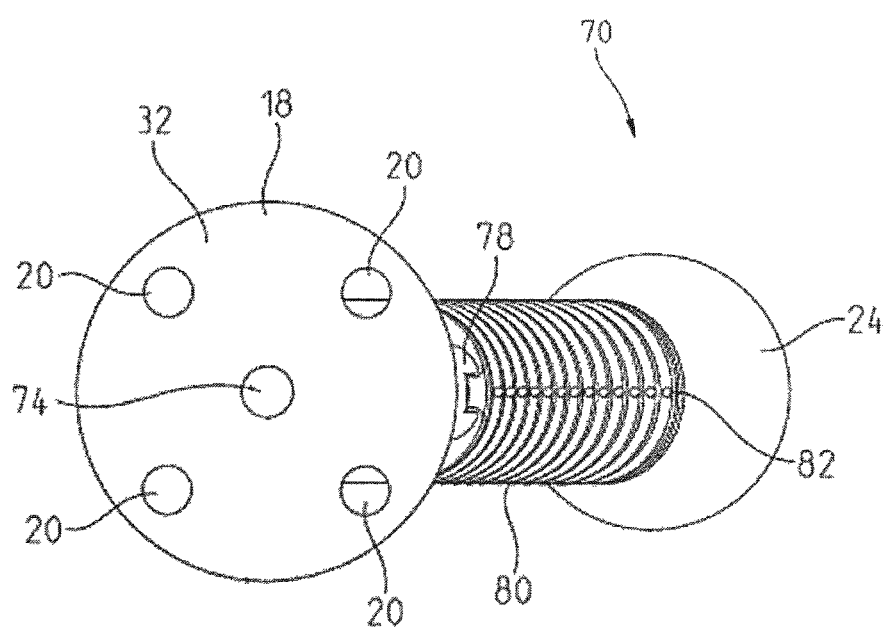
FIG. 7 is an end view of an obstetrical instrument according to the embodiment illustrated in FIG. 6.
Figure 8:
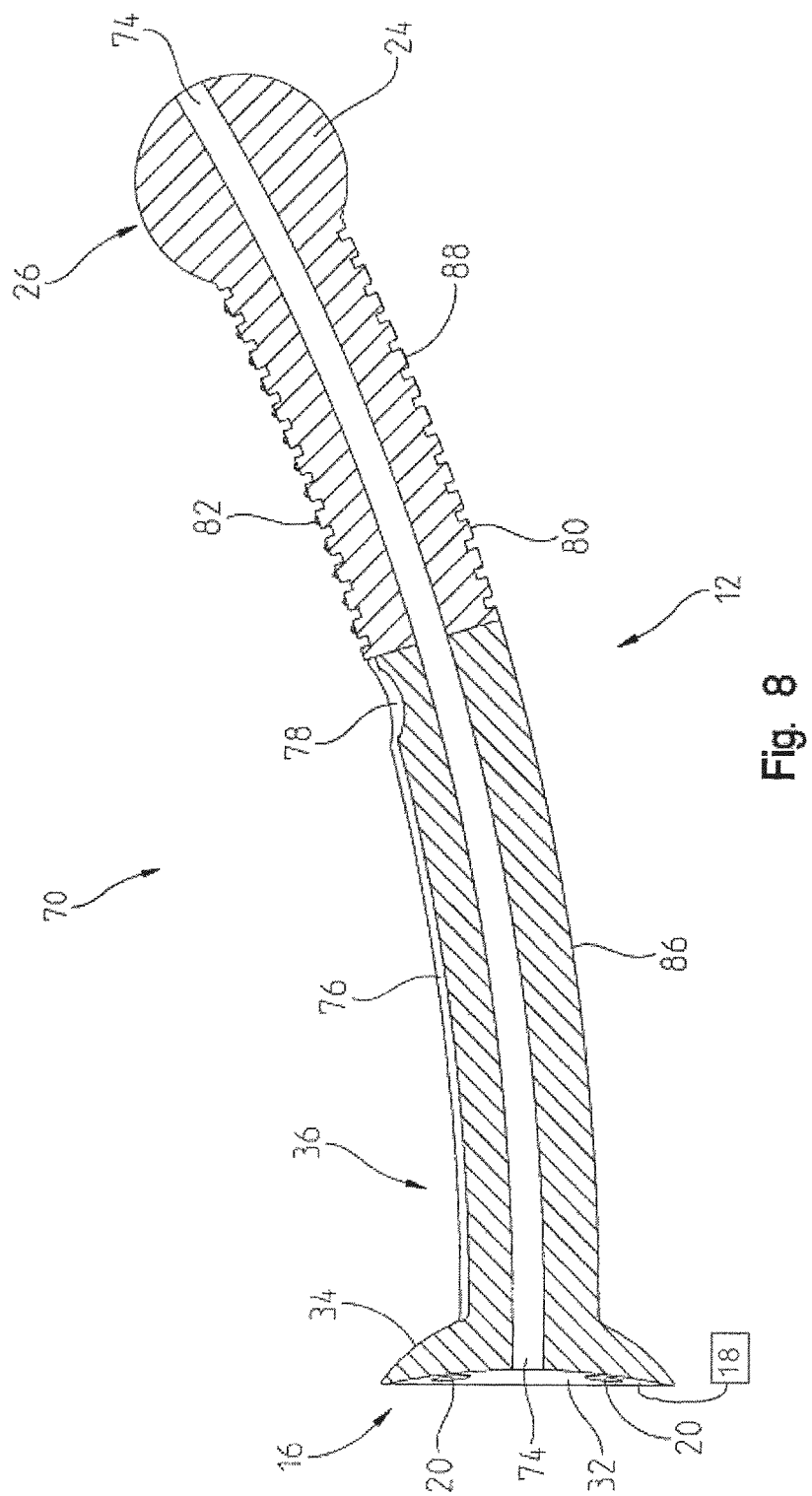
FIG. 8 is a cross-sectional view of another obstetrical instrument according to the present disclosure.

Referring now to FIGS. 6-8, another obstetrical instrument 70 is illustrated. Obstetrical instrument 70 is similar to obstetrical instrument 10 illustrated in FIG. 1 and may include any or all of the features of obstetrical instrument 10. The same numerals used to refer to components of obstetrical instrument 10 are used to refer to similar components of obstetrical instrument 70. In some exemplary embodiments, obstetrical instrument 70 includes a fetal head support portion 14 as described above, the fetal head support portion 14 being coupled to the flared portion 18 of obstetrical instrument 70.

Obstetrical instrument 70 illustratively includes an elongated handle 12 and a flared portion 18 extending from the elongated handle 12. Obstetrical instrument 70 includes a curve from proximal end 26 to distal end 16 to accommodate the natural curvature of a pelvis.

As shown in FIG. 6, the flared portion 18 includes a distal face 32 sized and structured to support and elevate a fetal head. The flared portion 18 includes a plurality of openings 20 extending from the distal face 32 to a proximal side 34 of the flared portion defining a fluid flow path through the flared portion. A fetal head supporting force applied by a user to elongated handle 12 is transmitted through the obstetrical instrument 70 and spread across the distal face 32 of the flared portion, thereby providing a more even distribution of force to the fetal head and reduced risk of injury to the fetus. The presence of the fluid flow path resists formation of a vacuum between the distal face 32 of the obstetrical instrument 70 and the fetal head.

Obstetrical instrument 70 further includes a groove 76 extending along an upper portion 36 along at least a portion of elongated handle 12 in a direction parallel with a longitudinal axis of the elongated handle 12. As illustrated in FIG. 6, the groove 76 provides a direction indictor to indicate the top of the obstetrical instrument 10, similar to ridge 30 in FIG. 1, allowing a user to orient the obstetrical instrument 10. The groove 76 is recessed into the body of handle 12, allowing for increased comfort for the patient, and a lower chance of the user inadvertently harming or lacerating maternal tissue upon insertion of obstetrical instrument 70. Additionally, the groove 76 provides a path for evacuating fluid through groove 76 to the plurality of circumferential ridges 80 in grip portion 28, which allows for a better grip on obstetrical instrument 70 by the user.

Obstetrical instrument 70 further includes a depression 78 on an upper portion 36 of elongated handle 12. As shown in FIG. 6, the depression is configured to receive a user's thumb, indicating to the user that his or her hand is in the correct position. In some embodiments, the depression 78 provides increased grip for the user, reduces slippage, and allows for positioning of the user's hand to provide appropriate leverage on the fetal head. It also provides direction regarding orientation, while depression 78 is illustrated in a portion of handle 12 that is without circumferential ridges 80, depression 78 could also be positioned in the portion of handle 12 over which circumferential ridges 80 are positioned.

As illustrated in FIGS. 6 and 7, elongated handle 12 further includes a plurality of indexing markers 82. Each indexing marker 82 is illustratively pronounced enough to be felt by a user through a medical glove. Although illustrated as raised dots in FIGS. 6 and 7, in other embodiments indexing markers 82 may be recessed into the elongated handle 12 or have a different shape, such as square, triangular, or rectangular. Indexing markers illustratively provide a directional indicator of the top of the obstetrical instrument 70, allowing a user to orient the obstetrical instrument 70. In addition, the depth of insertion of the obstetrical instrument 70 into the patient can be determined by monitoring (such as by sight or touch) the number of indexing markers 82 that have not been inserted into the patient.

As shown in FIG. 8, aperture 74 illustratively extends as a conduit fluidly connecting the distal end 16 to the proximal end 26 through obstetrical instrument 70. The fluid connection allows for a fluid, such as air, to flow freely through the obstetrical instrument 70 such that no vacuum is created between obstetrical instrument 70 and the head of a fetus during use by a practitioner.

In some exemplary embodiments, the elongated handle 12 is formed from a single piece. In other embodiments, such as shown in FIG. 8, the elongated handle 12 of obstetrical instrument 70 is illustratively formed from multiple pieces, such as a distal portion 86 and a proximal portion 88. As shown in FIG. 8, distal portion 86 illustratively includes flared portion 18, groove 76, and depression 78 and proximal portion illustratively includes circumferential ridges 80, indexing markers 82, and bulbous portion 24. Distal portion 86 and proximal portion 88 are rigidly connected by any suitable means including adhesive, corresponding male and female threads, and a fixation ring and/or at least one flange between distal portion 86 and proximal portion 88.

Figure 9:
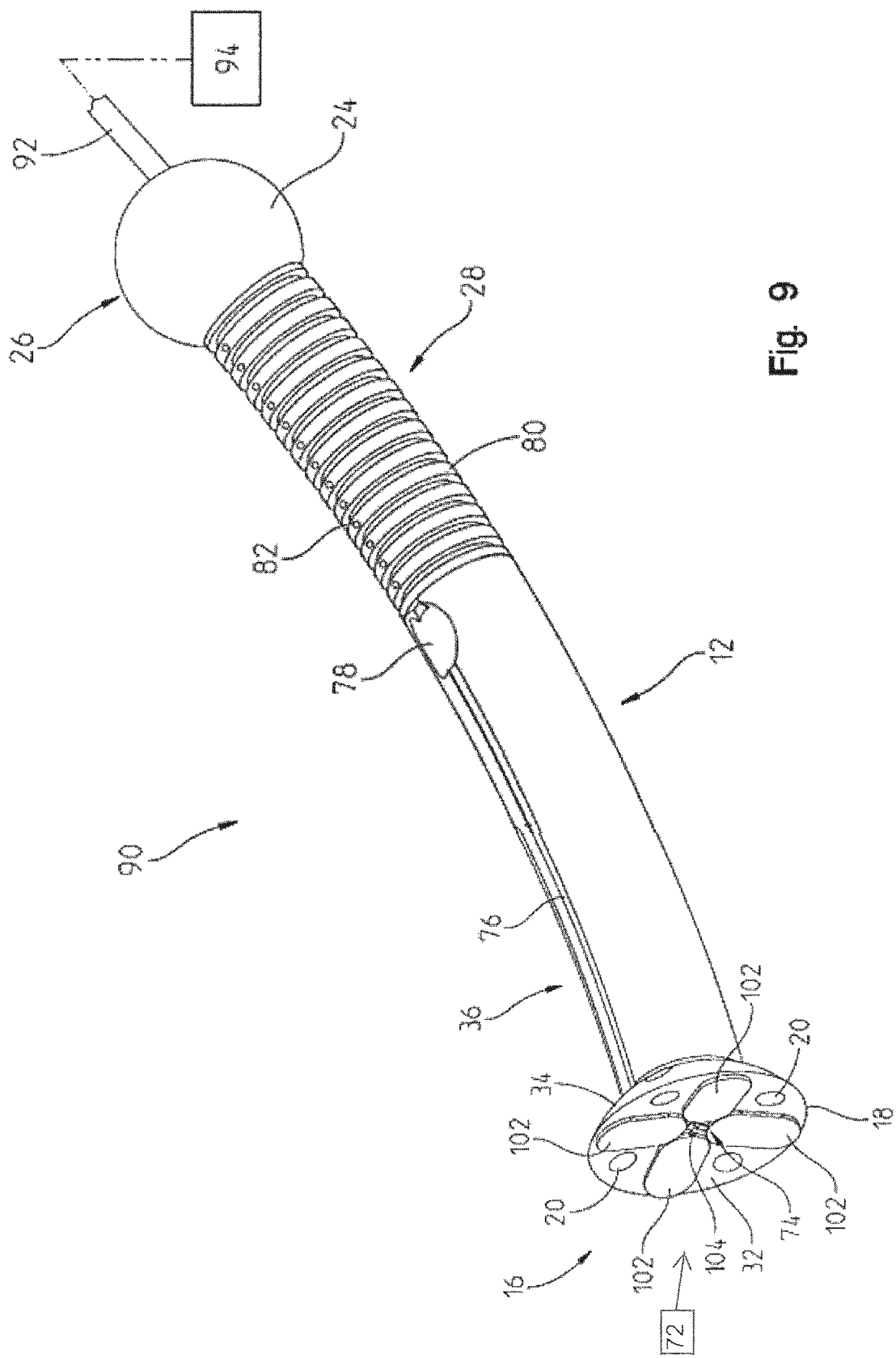
FIG. 9 is a perspective view of still another embodiment of an obstetrical instrument according to the present disclosure.

Referring next to FIG. 9, another obstetrical instrument 90 is illustrated. Obstetrical instrument 90 is similar to obstetrical instrument 70 illustrated in FIGS. 6-8 and may include any or all of the features of obstetrical instruments 70. The same numerals used to refer to components of obstetrical instrument 70 are used to refer to similar components of obstetrical instrument 90. In some exemplary embodiments, obstetrical instrument 90 includes a fetal head support portion 14 as described above, the fetal head support portion 14 being coupled to the flared portion 18 of obstetrical instrument 90.

Referring next to FIGS. 10-13, another obstetrical instrument 100 is illustrated. Obstetrical instrument 100 is similar to obstetrical instrument 70 illustrated in FIGS. 6-8, and obstetrical instrument 100 illustrated in FIG. 9, and may include any or all of the features of obstetrical instruments 70, and/or 90. The same numerals used to refer to components of obstetrical instruments 70, and 90 are used to refer to similar components of obstetrical instrument 100. In some exemplary embodiments, obstetrical instrument 100 includes a fetal head support portion 14 as described above, the fetal head support portion 14 being coupled to the flared portion 18 of obstetrical instrument 100.

As shown in FIGS. 9-13, the distal end 16 of obstetrical instrument 90 and obstetrical instrument 100 each include a pressure sensor 72, illustratively a plurality of pressure pads 102. Although illustrated as including four pressure pads 102 in FIGS. 9-13, in other embodiments pressure sensor 72 includes one, two, three, five, or more pressure pads 102 in any suitable arrangement.

In the exemplary embodiment of obstetrical instrument 90 illustrated in FIG. 9, each pressure pad 102 is operatively connected by one or more wires 92 that extends through aperture 74 to pressure sensor control unit 94. Pressure sensor 72 is configured to provide a pressure measurement on pressure sensor control unit 94 indicating to a user the force being exerted by obstetrical instrument 90 on the head of the fetus.

In the exemplary embodiment of obstetrical instrument 100 illustrated in FIGS. 10-13, each pressure pad 102 is operatively connected by a wire 104 that extends through aperture 74 to transmitter 106, powered by battery 108. Transmitter 106 illustratively sends a wireless transmission to a receiver of a control unit (not shown), which is configured to provide a pressure measurement indicating to a user the force being exerted by obstetrical instrument 100 on the head of the fetus. In some embodiments, the control unit provides separate pressure measurements for each pressure pad 102. The separate pressure measurements may allow a user to better position the device to allow greater contact area with the fetal head, which allows for a more even distribution of force and reduced risk of injury to the fetus. In one more particular embodiment, the control unit is configured to issue a warning, such as a visual or audio warning, to the user if the value of one or more pressure measurements exceeds a predetermined level.

Figure 12:
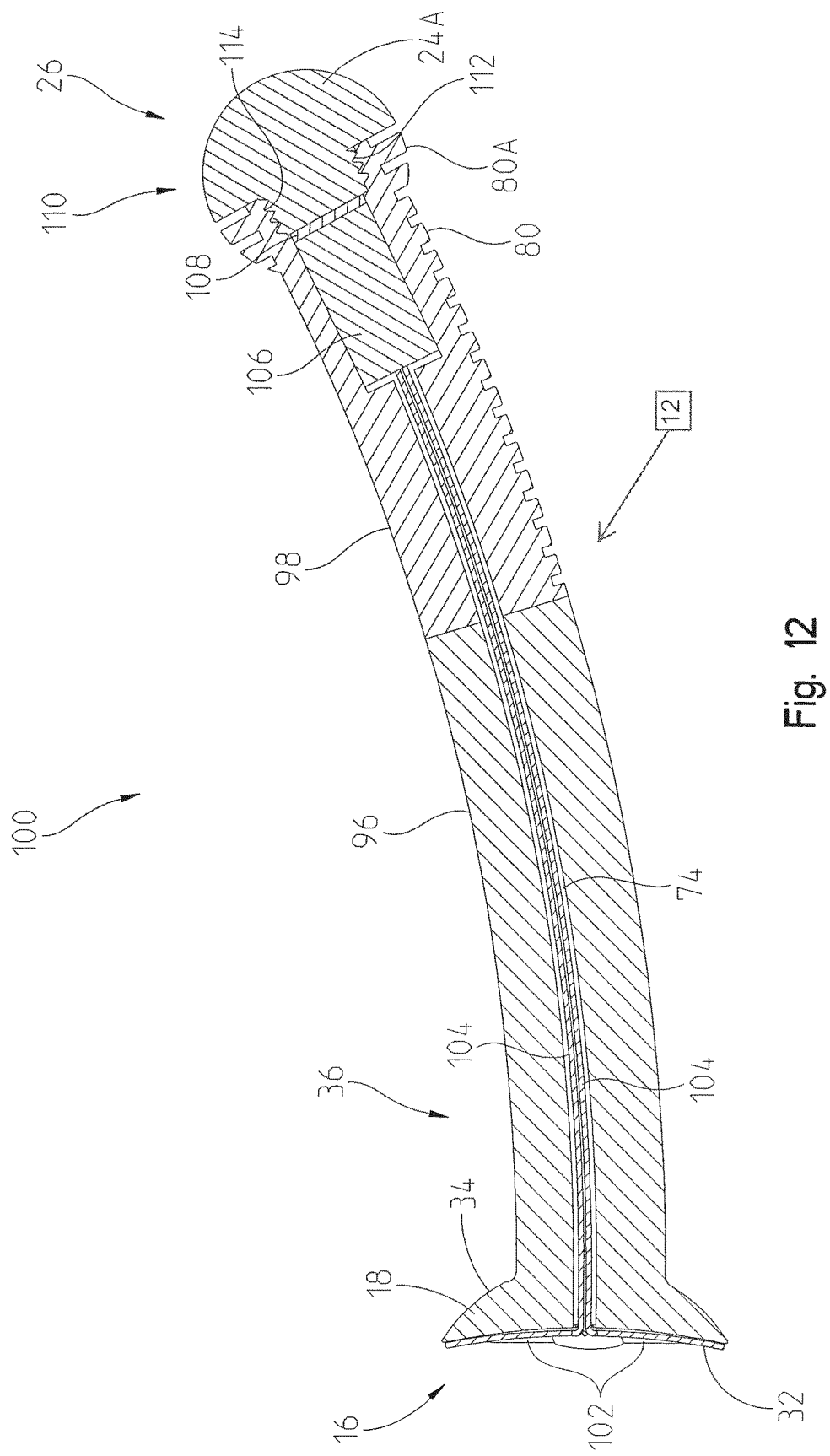
FIG. 12 is a cross-sectional view of the obstetrical instrument according to the embodiment illustrated in FIG. 10.
Figure 13:
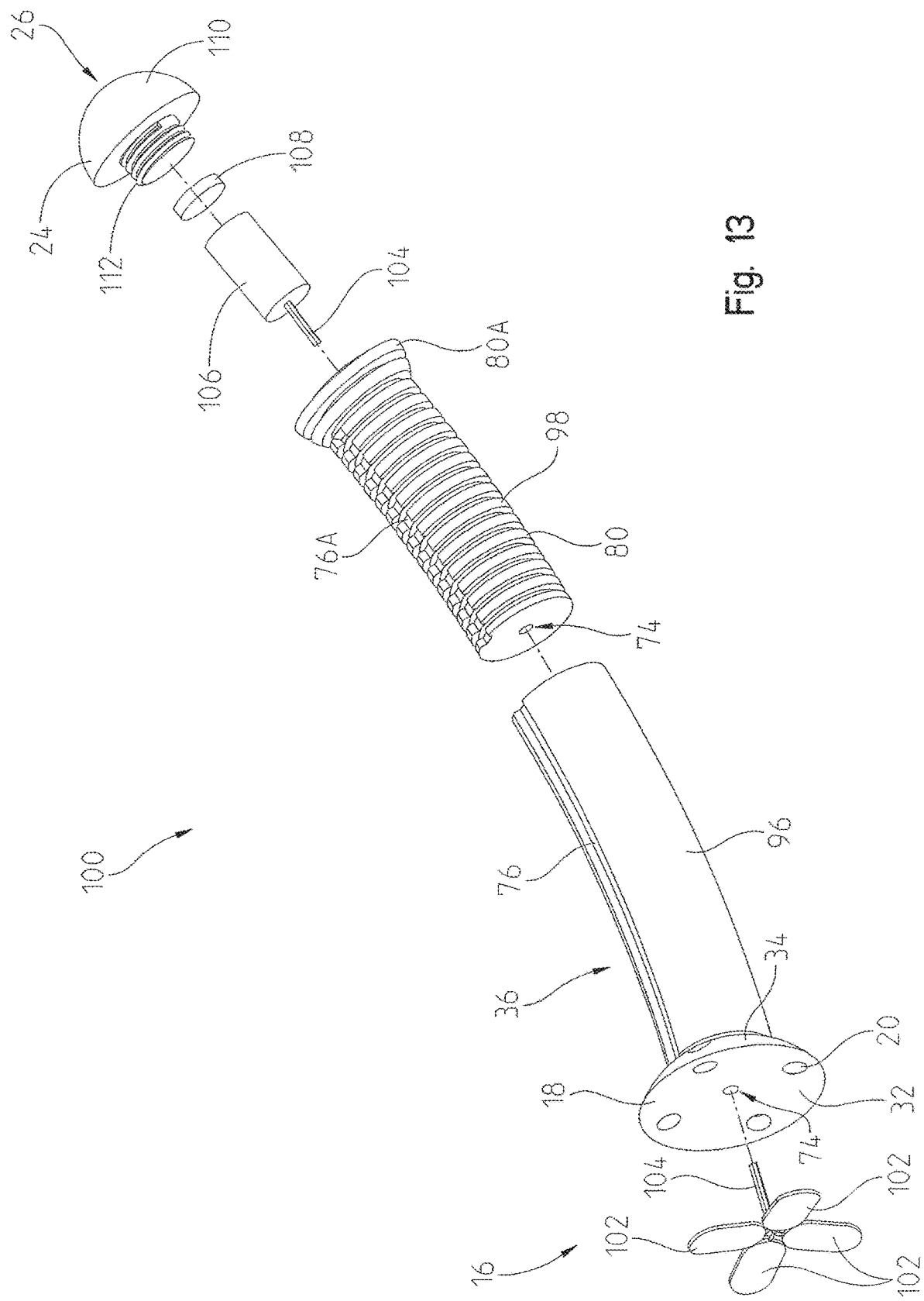
FIG. 13 is an exploded view of the obstetrical instrument according to the embodiment illustrated in FIG. 10.

As shown in FIGS. 12 and 13, elongated handle 12 includes a distal portion 96 and a proximal portion 98. Aperture 74 illustratively forms a conduit through distal portion 96 and proximal portion 98 to operatively connect the pressure pads 102 with transmitter 106. Distal portion 96 and proximal portion 98 are rigidly connected by any suitable means including adhesive, corresponding male and female threads, and a fixation ring and/or at least one flange between distal portion 96 and proximal portion 98. Handle 12 may, in an alternative embodiment may be formed in a single piece.

Figure 10:
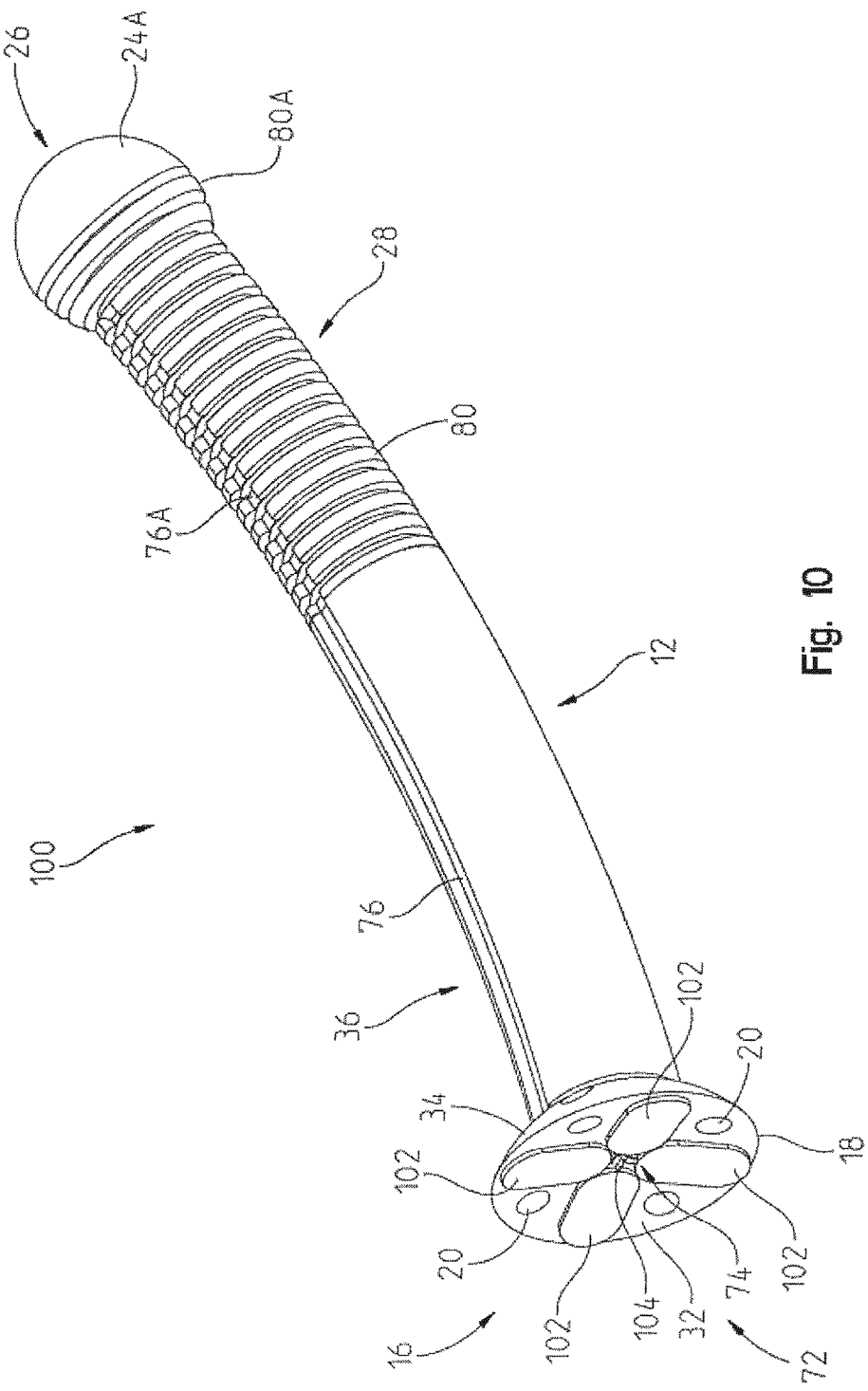
FIG. 10 is a perspective view of yet still another embodiment of an obstetrical instrument according to the present disclosure.
Figure 10A:
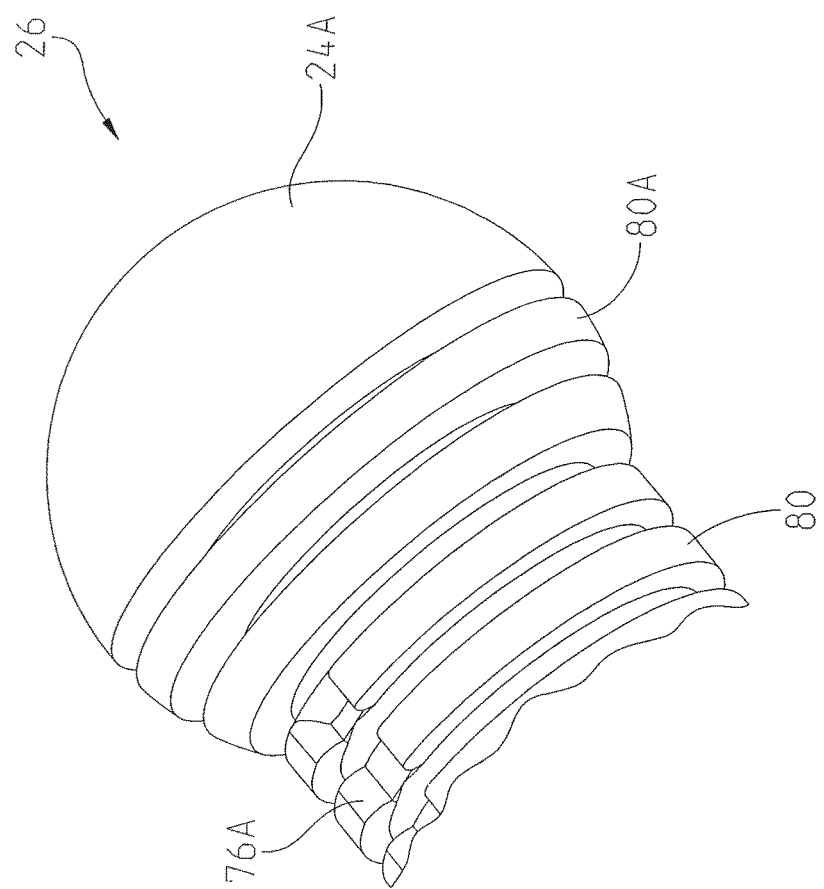
FIG. 10A is an enlarged view of the proximal end of the obstetrical instrument illustrated in FIG. 10.
Figure 11:
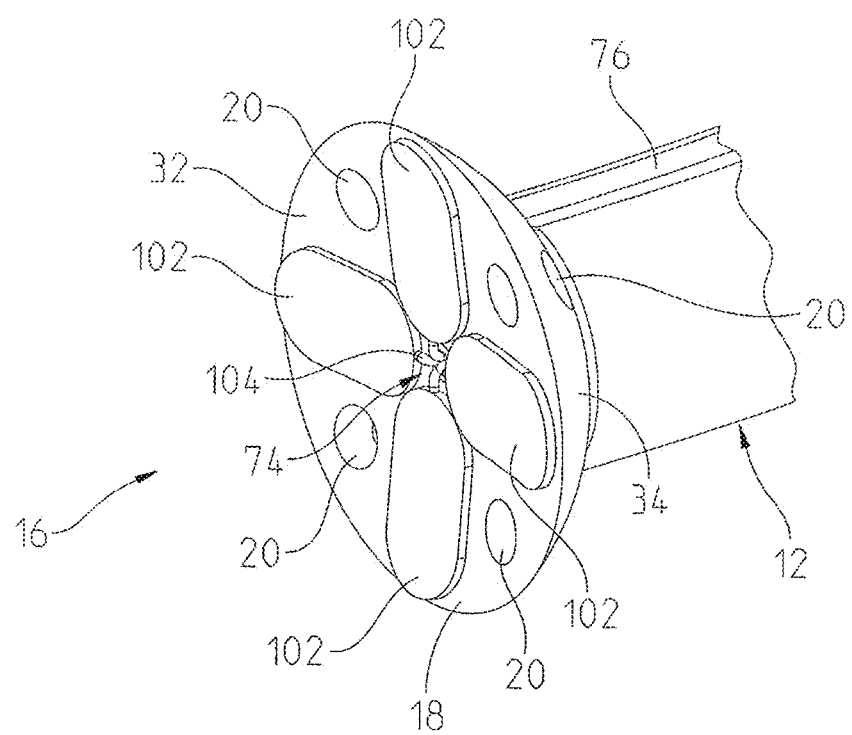
FIG. 11 is an enlarged view of the distal end of the obstetrical instrument illustrated in FIG. 10.

As illustrated in FIGS. 10 and 13, obstetrical instrument 100 includes a groove 76 extending along at least a portion of distal portion 96 and groove 76A extending along at least a portion of proximal portion 98 in a direction parallel with a longitudinal axis of the elongated handle 12. Groove 76A is illustratively formed in the plurality of circumferential ridges 80 in the grip portion 28. Grooves 76, 76A provide a direction indictor to indicate the top of the obstetrical instrument 100, allowing a user to orient the obstetrical instrument 100. Grooves 76 and 76A further provide a path for evacuating fluid to the grooves formed by the plurality of circumferential ridges 80 in grip portion 28 and ridges 80A in the bulbous portion 24A of the proximal end 26 (see FIG. 10A), which allows for a better grip on obstetrical instrument 100 by the user.

Referring next to FIGS. 12 and 13, obstetrical instrument 100 illustratively includes a removable cap 110. Removable cap 110 allows access to transmitter 106 and battery 108 in the interior of proximal portion 98. Removable cap 110 is illustratively removably coupled to the proximal portion 98 through mating threads 112 on removable cap 110 and mating threads 114 on proximal portion 98. In other embodiments, removable cap 110 is removably coupled to the proximal portion 98 through a friction fitting, a twist lock, a bayonet connection, a button press, or other suitable methods of attachment.

Figure 14:
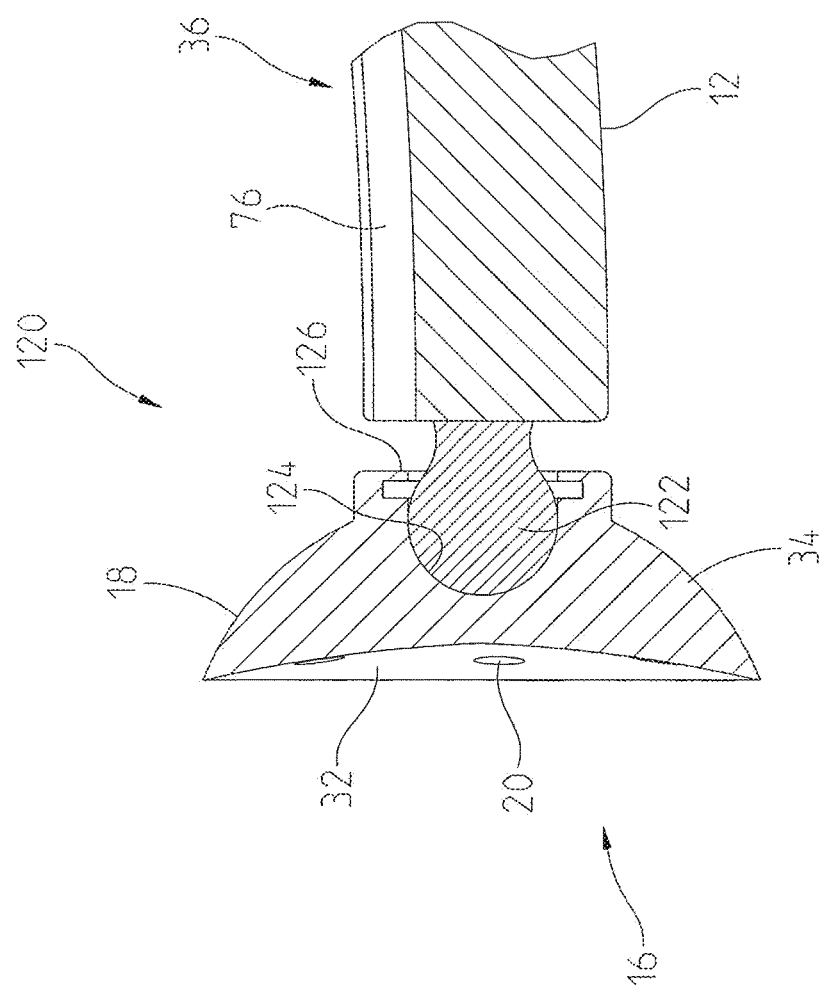
FIG. 14 is a cross-sectional view of the distal end of another obstetrical instrument according to the present disclosure.

Referring next to FIG. 14, another obstetrical instrument 120 is illustrated. Obstetrical instrument 120 is similar to obstetrical instrument 70 illustrated in FIGS. 6-8, obstetrical instrument 90 illustrated in FIG. 9, and obstetrical instrument 100 illustrated in FIGS. 10-13, and may include any or all of the features of obstetrical instruments 70, 90, and/or 100. The same numerals used to refer to components of obstetrical instruments 70, 90 and 100 are used to refer to similar components of obstetrical instrument 120. In some exemplary embodiments, obstetrical instrument 120 includes a fetal head support portion 14 as described above, the fetal head support portion 14 being coupled to the flared portion 18 of obstetrical instrument 120.

As shown in FIG. 14, the flared portion 18 is adjustably attached to the elongated handle 12. Although illustratively connected by a rotatable connection, such as the ball 122 and socket 124 shown in FIG. 14, other suitable adjustable connections are also possible. A deformable connector 126, such as flexible or deformable flange, maintains the attachment between the ball 122 and socket 124. The use of an adjustable connection, such as the ball 122 and socket 124 illustrated in FIG. 14 allows for a user to adjust the angle between the flared portion 18 and handle 12 to position the flared portion 18 as desired.

Figure 15:
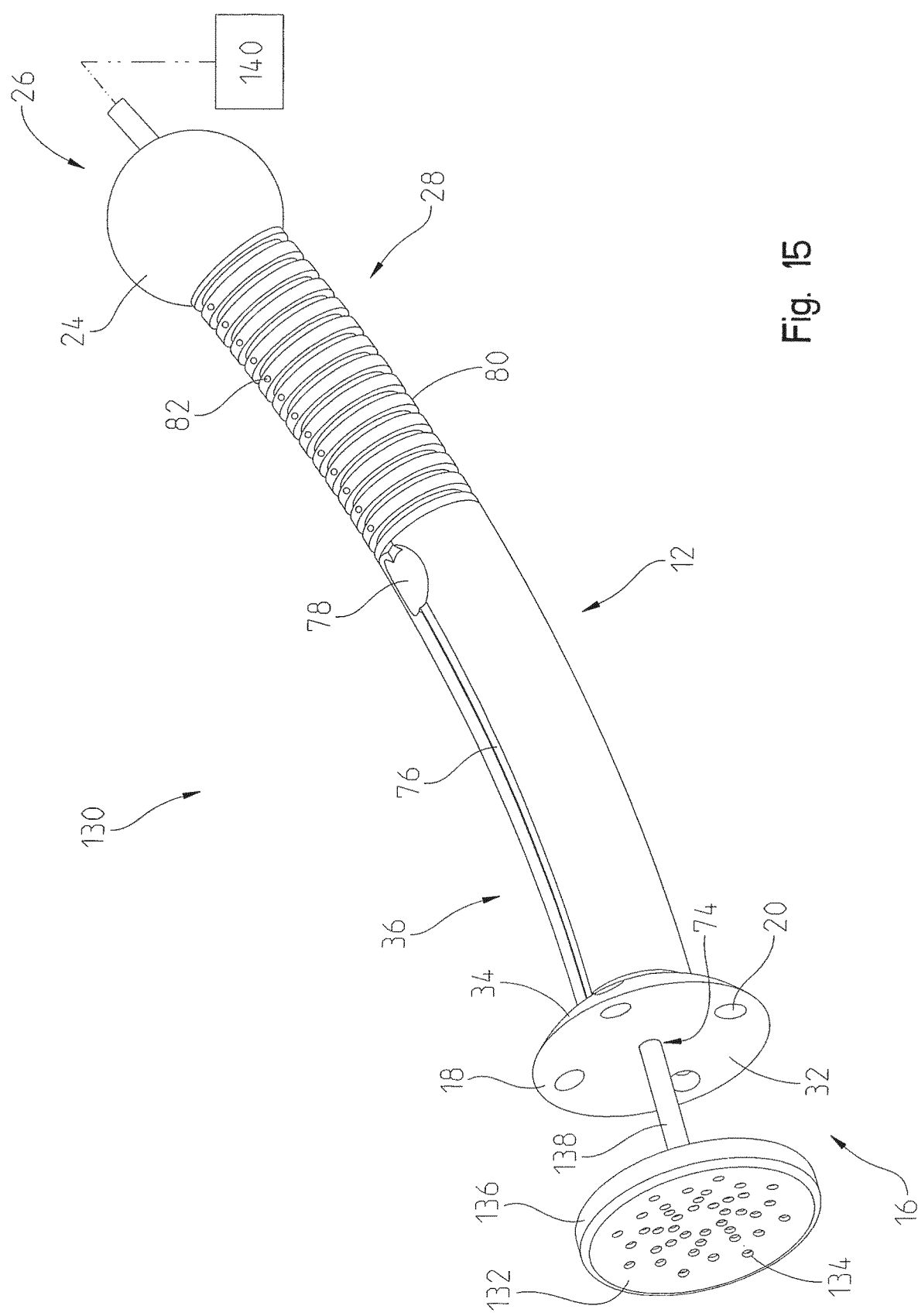
FIG. 15 is a perspective view of another embodiment of still another obstetrical instrument according to the present disclosure.

Referring next to FIG. 15, another obstetrical instrument 130 is illustrated. Obstetrical instrument 130 is similar in some respects to obstetrical instrument 70 illustrated in FIGS. 6-8, obstetrical instrument 90 illustrated in FIG. 9, obstetrical instrument 100 illustrated in FIGS. 10-13, and obstetrical instrument 120 illustrated in FIG. 14, and may include any or all of the features of obstetrical instruments 70, 90, 100 and/or 120. The same numerals used to refer to components of obstetrical instruments 70, 90, 100, and 120 are used to refer to similar components of obstetrical instrument 130. Obstetrical instrument 130 includes a fetal vacuum assist tool for assisting in an attempted vaginal delivery, and can also function as a fetal head elevator if the vaginal delivery fails and a cesarean delivery is initiated.

Obstetrical instrument 130 includes a groove 76 extending along at least a portion of elongated handle 12 in a direction parallel with a longitudinal axis of the elongated handle 12. The groove 76 is recessed into the body of handle 12, providing a path for evacuating fluid through groove 76 to the grooves formed between the plurality of circumferential ridges 80 in grip portion 28, which allows for a better grip on obstetrical instrument 130 by the user. Obstetrical instrument 130 further includes a depression 78 on an upper portion 36 of elongated handle 12 as described above, indicating to the user that his or her hand is in the correct position. Elongated handle 12 further includes a plurality of indexing markers 82 to provide a directional indicator of the top of the obstetrical instrument 130, allowing a user to orient the obstetrical instrument 130.

Obstetrical instrument 130 includes a vacuum extractor 132. Vacuum extractor 132 includes a plurality of openings 134 in a suction head 136 in fluid connection with a vacuum source 140 through a vacuum tube 138. Vacuum tube 138 is illustratively positioned through an aperture 74 running through elongated handle 12 of obstetrical instrument 130. In one embodiment, the aperture 74 is larger than the vacuum tube, allowing the elongated handle 12 to slide along the vacuum tube to change the distance between the suction head 136 and the flared portion 18 of obstetrical instrument 130.

The suction head 136 is initially positioned in contact with the fetal head and a vacuum assisted vaginal delivery is attempted. If the patient fails to deliver the baby vaginally, the flared portion 18 of obstetrical instrument 130 is positioned against the proximal end of the suction head 136, and the obstetrical instrument 130 is utilized as a fetal head elevator to assist in positioning the fetal head for a caesarian delivery, as described in detail above. In the event that vaginal delivery is abandoned and instrument 130 is used as a fetal head elevator in a caesarian delivery, then vacuum is no longer applied through suction head 136 to the fetus. In an alternative embodiment, a slight positive pressure can be applied through suction head 136 when instrument 130 is used as a fetal head elevator. In this way, suction between suction head 136 and the fetus is allowed to be broken when instrument 130 is used as a fetal head elevator. In a further alternative embodiment, suction head 136 can be removed from vacuum tube 138 prior to using instrument 130 as a fetal head elevator, with flared portion 18 being utilized to contact the fetus during elevation of the same, with apertures 20 working to eliminate the opportunity for a vacuum to form between instrument 130 and the fetus.

Figure 17:
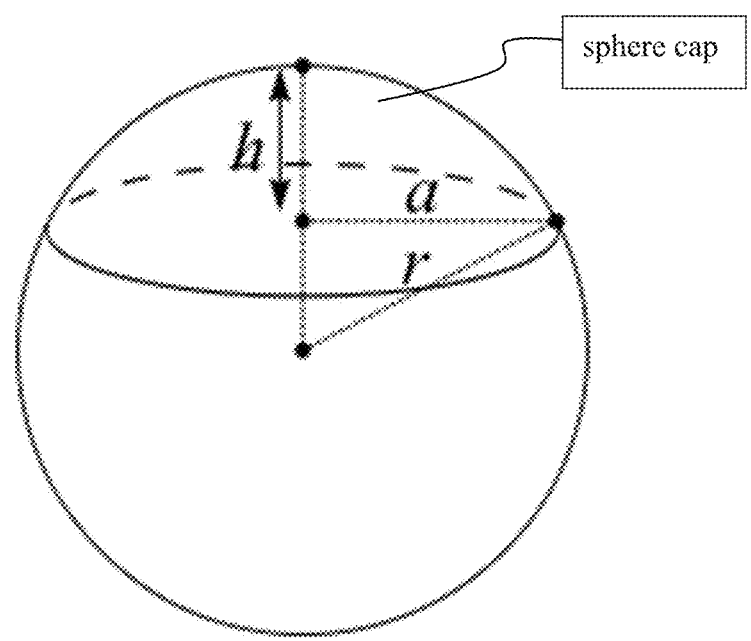
FIG. 17 is an illustration of a sphere and the components of a sphere cap thereof.

In an exemplification, the distal face of any of the obstetrical instruments disclosed herein (i.e., the portion intended to contact the fetus) can provide a contact area of about 7.4 in$^2$ (4774 mm$^2$). In alternative embodiments, the distal face can provide a contact area of about 7.0 in$^2$ (4516 mm$^2$), about 7.1 in$^2$ (4581 mm$^2$), about 7.2 in$^2$ (4645 mm$^2$), about 7.3 in$^2$ (4710 mm$^2$), about 7.4 in$^2$ (4774 mm$^2$), about 7.5 in$^2$ (4839 mm$^2$), about 7.6 in$^2$ (4903 mm$^2$), about 7.7 in$^2$ (4968 mm$^2$), or about 7.8 in$^2$ (5032 mm$^2$), or about or any range within any two of the foregoing values. In one particular embodiment, the distal face is in the form of a sphere cap with dimensions r=177.8 mm, h=4.6 mm and a=40 mm, with "r" denoting the radius of the sphere, "a" denoting the measure of the base radius of the plane intersecting the sphere and defining the sphere cap and "h" denoting the height of the sphere cap. For clarity, these dimensions are marked in FIG. 17. In this embodiment, the distal face would provide an area of 7.9 in$^2$ (5093 mm$^2$) if it were not interrupted. In an exemplification, the distal face is interrupted by 4 holes extending through the distal face, with each hole removing 0.13 in$^2$ (81.7 mm$^2$) of the distal face contact area, yielding an available distal face contact area of 4766.2 mm$^2$ (about 7.4 in$^2$). In spherical embodiments, the radius of the sphere may be, for example, 60 mm or 80 mm. The dimensions mentioned in this paragraph are merely exemplary and are not meant to be limiting in any way. In spherical embodiments, the radius of the sphere may be, for example, 60 mm or 80 mm. The dimensions mentioned in this paragraph are merely exemplary and are not meant to be limiting in any way. In certain embodiments, interchangeable heads with differing contact areas may be provided in different colors to facilitate selection based on maternal and fetal habitus. In one-piece embodiments, color may similarly be used to denoted fetal contact area size across a family of differently sized instruments.

Figure 16:
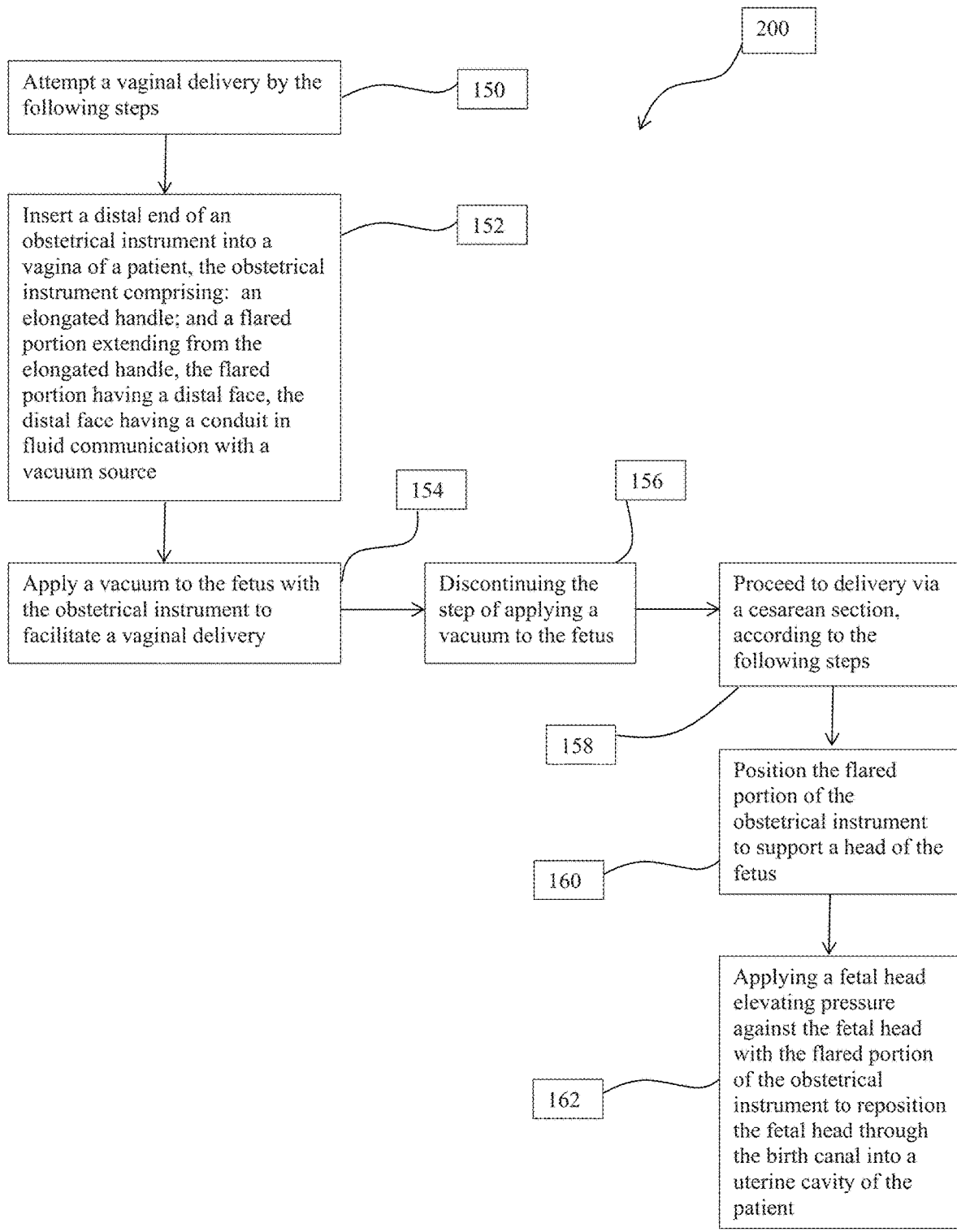
FIG. 16 is a flow chart depicting a method of delivering a fetus in accordance with an embodiment of the present disclosure.

FIG. 16 illustrates method 200 in accordance with an embodiment of the present disclosure. Method 200 begins at step 150 with an attempt at delivering a fetus vaginally. The delivery attempt of step 150 is specified in steps 152 and 154 with step 152 comprising inserting a distal end of an obstetrical instrument into a vagina of a patient, the obstetrical instrument comprising: an elongated handle; and a flared portion extending from the elongated handle, the flared portion having a distal face, the distal face having a conduit in fluid communication with a vacuum source; and step 154 comprising applying a vacuum to the fetus with the obstetrical instrument to facilitate a vaginal delivery. Method 200 continues at step 156 with the step of discontinuing the step of applying a vacuum to the fetus. At step 158, a cesarean section is used to deliver the fetus. The delivery at step 158 is specified in steps 160 and 162 with step 160 comprising positioning the flared portion of the obstetrical instrument to support a head of the fetus, and step 162 comprising applying a fetal head elevating pressure against the fetal head with the flared portion of the obstetrical instrument to reposition the fetal head through the birth canal into a uterine cavity of the patient.

Although the obstetrical instrument of the present invention has been described for use in a childbirth environment, it may have additional applications in the veterinary field for the comparative birthing process.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

The invention claimed is:

1. An obstetrical instrument comprising:
an elongated handle;
a flared portion extending from said elongated handle, said flared portion having a distal face defining a perimeter, the distal face sized and structured to support and elevate a fetal head, wherein the flared portion defines a fluid flow path from the distal face to an exterior of the flared portion, such that, with the obstetrical instrument positioned to support and elevate the fetal head, a fetal head elevating force transmitted through the obstetrical instrument is spread across the distal face of the flared portion and wherein the fluid flow path presents a gap in the distal face within the perimeter of the flared portion, the gap defining an area within the perimeter that does not contact the fetal head, the gap resisting formation of a vacuum between the flared portion and a fetal head supported by the obstetrical instrument; and
a pressure sensor positioned to measure a positive pressure indicative of the fetal head elevating force applied to the fetal head by the obstetrical instrument.

2. The obstetrical instrument of claim 1, further comprising a battery and a transmitter operatively coupled to the pressure sensor and configured to be positioned in an interior cavity of the elongated handle, the transmitter configured to wirelessly transmit a signal indicating a measured pressure to an external receiver.

3. The obstetrical instrument of claim 1, further comprising a wire extending through a conduit from the pressure sensor to a proximal end of the elongated handle, the wire configured to transmit a signal indicating a measured pressure from the pressure sensor to an external receiver.

4. The obstetrical instrument of claim 1, wherein the pressure sensor comprises a plurality of pressure pads positioned on the distal face of the flared portion.

5. The obstetrical instrument of claim 1, wherein the elongated handle includes a recessed groove extending from the flared portion along an upper portion of the elongated handle.

6. The obstetrical instrument of claim 1, wherein the elongated handle further includes a grip portion comprising a plurality of grooves defined between a plurality of circumferential ridges, the recessed groove extending from the flared portion through at least a portion of the grip portion.

7. The obstetrical instrument of claim 1, wherein the elongated handle includes at least one directional indicator selected from the group consisting of: a recessed groove extending from the flared portion along an upper portion of the elongated handle; a depression in the elongated handle configured to receive a user's thumb; and a plurality of indexing markers positioned on a plurality of ridges of the elongated handle.

8. The obstetrical instrument of claim 1, wherein the elongated handle further includes a bulbous portion, at least a portion of the bulbous portion comprising a plurality of grooves defined between a plurality of circumferential ridges.

9. The obstetrical instrument of claim 1, wherein the flared portion is rotatably affixed to the elongated handle.

10. The obstetrical instrument of claim 1, wherein the elongated handle includes a conduit defining a fluid passageway extending from a distal end of the elongated handle to a proximal end of the elongated handle.

11. An obstetrical instrument comprising:
an elongated handle;
a flared portion extending from said elongated handle, said flared portion having a distal face defining a perimeter, the distal face sized and structured to support and elevate a fetal head, wherein the flared portion defines a fluid flow path from the distal face to an exterior of the flared portion, such that, with the obstetrical instrument positioned to support and elevate the fetal head, a fetal head elevating force transmitted through the obstetrical instrument is spread across the distal face of the flared portion and wherein the fluid flow path presents a gap in the distal face within the perimeter of the flared portion, the gap defining an area within the perimeter that does not contact the fetal head, the gap resisting formation of a vacuum between the flared portion and a fetal head supported by the obstetrical instrument;
wherein the elongated handle includes at least one directional indicator extending radially from a longitudinal axis of the elongated handle to denote a rotational orientation of the obstetrical instrument, the at least one directional indicator includes a recessed groove extending from the flared portion along an upper portion of the elongated handle and a depression in the elongated handle configured to receive a user's thumb.

12. The obstetrical instrument of claim 11, wherein the at least one directional indicator includes a plurality of indexing markers positioned on a plurality of ridges of the elongated handle.

13. The obstetrical instrument of claim 11, wherein the flared portion is rotatably affixed to the elongated handle.

14. The obstetrical instrument of claim 11, wherein the elongated handle includes a conduit defining a fluid passageway extending from a distal end of the elongated handle to a proximal end of the elongated handle.

15. An obstetrical instrument comprising:
an elongated handle including a conduit extending from and through a distal end of the elongated handle to and through a proximal end of the elongated handle;
a flared portion extending from said elongated handle, said flared portion defining a perimeter and having a distal face sized and structured to support and elevate a fetal head;
wherein the flared portion includes an opening within the perimeter of the flared portion, the opening in fluid communication with the conduit defining a fluid flow path through the flared portion and the elongated handle such that, with the obstetrical instrument positioned to support and elevate the fetal head, a fetal head elevating force transmitted through the obstetrical instrument is spread across the distal face of the flared portion and whereby the fluid flow path resists formation of a vacuum between the flared portion and a fetal head supported by the obstetrical instrument, the distal face defining a contact surface area within the perimeter available to contact the fetal head, the contact surface area larger than an area of the opening.

16. An obstetrical instrument comprising:
an elongated handle;
a flared portion extending from said elongated handle, said flared portion having a distal face sized and structured to support and elevate a fetal head; and
a suction head including a plurality of openings in fluid communication with a vacuum source, said suction head sized and structured to assist in a vacuum assisted vaginal delivery wherein the plurality of openings are distally presented so that the plurality of openings are available for fluid communication with the fetal head.

17. The obstetrical instrument of claim 16, further comprising a vacuum tube fluidly connecting the suction head with the vacuum source, at least a portion of the vacuum tube being positioned in a conduit extending from a distal end of the elongated handle to a proximal end of the elongated handle.

18. The obstetrical instrument of claim 16, wherein the flared portion includes a second plurality of openings within a circumference of the flared portion, the second plurality of openings extending from the distal face to a proximal side of the flared portion and defining a fluid flow path therethrough.

19. The obstetrical instrument of claim 16, further comprising a depression in the elongated handle configured to receive a user's thumb.

20. An obstetrical instrument, comprising:
an elongated handle; and
a flared portion extending from said elongated handle, said flared portion having a distal face sized and structured to support and elevate a fetal head, whereby the fetal head can be supported and elevated by the flared portion in the birth canal prior to delivery, the distal face defining a perimeter, said flared portion defining a fluid flow path from said distal face of said flared portion to an exterior of said flared portion, said fluid flow path presenting a gap in the distal face within the perimeter of the distal face so that, with the obstetrical instrument positioned to support and elevate the fetal head, the gap defines an area within the perimeter of the distal face that does not contact the fetal head, whereby the fluid flow path resists formation of a vacuum between the obstetrical instrument and a fetal head supported by the obstetrical instrument;
wherein the elongated handle includes a socket for receiving a ball coupled to the flared portion for coupling the flared portion to the elongated handle.

21. The obstetrical instrument of claim 20, wherein the elongated handle has a length sized to allow pressure to be applied from a user's hand holding the handle to the fetal head to reposition the fetal head through a birth canal into a uterine cavity.

22. The obstetrical instrument of claim 20, wherein the distal face defines a contact surface area within the perimeter available to contact the fetal head, the contact surface area larger than the area of the gap, whereby a fetal head elevating force transmitted through the obstetrical instrument is spread across the contact surface area.

* * * * *